//  
United States Patent [19]
Pohler

[11] 4,442,403
[45] Apr. 10, 1984

[54] TESTING INSTALLATION FOR PIPES HAVING AN INTERNAL TESTING UNIT DRIVEN BY THE ROTATION OF THE PIPE

[76] Inventor: Carl-Ludwig Pohler, Lutzowstrasse 123, D-5650 Solingen 1, Fed. Rep. of Germany

[21] Appl. No.: 249,887

[22] Filed: Apr. 1, 1981

[51] Int. Cl.$^3$ ............... G01N 27/72; G01N 27/82; G01R 33/12
[52] U.S. Cl. ............... 324/220; 324/226; 324/262
[58] Field of Search ............... 324/219–221, 324/262, 226; 73/623

[56] References Cited

U.S. PATENT DOCUMENTS

| | | | |
|---|---|---|---|
| 3,535,623 | 10/1970 | Wood et al. | 324/220 |
| 4,217,548 | 8/1980 | Furukawa et al. | 324/220 |
| 4,247,819 | 1/1981 | Shimada et al. | 324/262 |

Primary Examiner—Gerard R. Strecker
Assistant Examiner—Walter E. Snow
Attorney, Agent, or Firm—Young & Thompson

[57] ABSTRACT

A testing installation for pipes and rod material to determine surface defects and/or core defects, comprises a plurality of test zones (1, 2) having a rotary roller track (3) for rotatingly driving the pipe (4) to be tested. An internal testing unit (7) is movable lengthwise of the pipe, within the pipe; and parking stations (9, 10) adjustable to the pipe length are provided at both ends of the testing zone for accommodating the internal testing unit during pipe change. An external testing unit (12) is movable along the outer pipe wall (11), and conveying devices (16) for the introduction and removal of the pipes into and from the testing zones are provided. The internal testing unit (7) is a cylindrical housing (21) having built-in contactless testing devices (22) and arranged on a running gear frame (23) with a forward running gear and a rearward running gear (24, 25). These running gears comprise a drive shaft (26) and two supporting rollers (27, 28) assuming a driving position (26′, 27′, 28′) obliquely to the longitudinal axis of the pipe to be tested and travelling on the inner pipe wall and being driven by the revolving motion of the pipe to be tested.

14 Claims, 7 Drawing Figures

TESTING INSTALLATION FOR PIPES HAVING AN INTERNAL TESTING UNIT DRIVEN BY THE ROTATION OF THE PIPE

For the testing of pipes of great lengths, for example 36 meters, for crack formations in the surface of the internal wall, testing devices are employed exhibiting an extension arm movable in the direction of the longitudinal pipe axis, an eddy-current-type testing device being arranged at the free end of this extension arm.

No devices have been known heretofore to perform simultaneous testing of pipes for cracks in the inner and outer wall surfaces.

The decisive disadvantage of the conventional testing arrangements for pipes to detect internal cracks resides in the large structural length and a correspondingly voluminous space requirement, due to the necessity of dimensioning the extension arm in correspondence with the maximum pipe length; as a consequence, the total structural length of the testing installation is determined by twice the maximum pipe length plus the longitudinal dimensions for the advance feed drive of the extension arm as well as the clamping device and optionally the revolving drive mechanism for the pipes to be tested.

The invention has as its objective to develop a testing installation for determining cracks in the inner and outer walls of pipes, which installation has a structural length substantially reduced as compared with the conventional pipe testing installations and makes it possible to perform comprehensive testing of the pipes for crack formations.

This object has been attained according to the invention by a testing installation for pipes exhibiting testing devices for determining surface defects of the inner and/or outer pipe walls. The testing installation of this invention is characterized by at least one testing zone with a rotary roller track for the revolving drive of the pipe to be tested, by an internal testing unit movable within the pipe in the direction of the longitudinal pipe axis, by parking or dwell stations adjustable to the pipe length at both ends of the testing zone to accommodate the internal testing unit during pipe change, by an external testing unit movable along the outer pipe wall, as well as by conveying means for introducing and for removing the pipes into and from the testing zone, wherein the internal testing unit exhibits a cylindrical housing with installed or built-in noncontactual testing devices or instruments, this housing being arranged on a running gear frame with a front and rear running gear, and wherein the running gears consist of a drive roller and two supporting rollers assuming a drive position obliquely to the longitudinal axis of the pipe to be tested, traveling along the inner pipe wall, and being driven by the revolving motion of the pipe to be tested, which pipe is arranged between the parking stations.

The testing installation is advantageously designed as a two-lane testing installation with two testing zones.

In another advantageous embodiment of the invention, the drive roller is arranged in the central longitudinal plane of the internal testing unit and exhibits a radial fixed adjustment with respect to the longitudinal axis of the internal testing unit, and the supporting rollers are adjustable radially with respect to the longitudinal axis of the testing unit in correspondence with the inner diameter of the pipe to be tested.

A substantial simplification of the invention is obtained by equipping the internal testing units with exchangeable running gears for varying pipe diameters, with a fixed setting for the drive position as well as the radial spacing of the drive roller and the supporting rollers with respect to the central longitudinal axis of the internal testing unit.

Another feature of the invention provides that the parking stations are fashioned as delivery or outlet tables with a roller guide means for receiving the internal testing unit as well as an advancing means for the testing unit. The advancing means for the internal testing unit is suitably designed as a lifting cylinder arranged on the delivery table.

In a first modified embodiment of the delivery table, the latter is equipped with a lifting device for hoisting the end of the roller guide means, fashioned as a pivoting guide, for the internal testing unit, which end faces away from the pipe to be tested, wherein a forward motion in the direction toward the pipe to be tested is imparted to the internal testing unit by the lifting of the roller guide means.

Advantageously, the delivery table, provided with the roller guide means designed as a pivoting guide, can be equipped with an additional lifting device for hoisting the end of the roller guide means adjacent to the pipe to be tested.

A further modified embodiment of the parking stations provides delivery tables with a roller belt guide for the internal testing unit, the two roller belts being drivable by a motor.

Another essential feature of the invention resides in the control of the forward and reverse travel of the internal testing unit by a change in the revolving direction of the motor-driven wobble disks of the rotary roller track.

A decisive advantage of the invention results from a fixed setting of the measuring distance between the testing devices of the internal testing unit and the inner wall of the pipe to be tested, which setting is independent of the diameter of the pipe to be tested, and which setting is obtained by way of the radial fixed adjustment of the drive roller of the running gears pertaining to the internal testing unit.

In another advantageous embodiment of the invention, the external testing unit comprises a carriage with built-in testing devices as well as marking devices movable along the carriage by a motor for identifying the internal and external defects and optionally the core defects of the pipe to be tested, wherein the motor-driven carriage is movable along the testing zone underneath the pipe in the region of the vertical longitudinal plane of symmetry thereof.

In a modified design of the testing installation, the external testing unit consists of a carriage with built-in testing devices for detecting the defects of the pipes, as well as with a separate conveyor cart traveling behind the carriage and comprising optionally motor-driven marking devices for identifying the defects of the pipes to be tested.

The conveyor carts for the marking devices can be coupled with the carriage for the testing devices or they can have a separate drive mechanism.

An essential feature of the invention finally resides furthermore in a control for the positionally accurate marking of the internal defects, external defects, and optionally core defects of the pipes to be tested, as determined by the internal testing unit and the external testing unit, which marking is executed on the outer pipe wall, wherein this control operates in such a way that the external testing unit, with the same advancing speed as the internal testing unit, travels over the testing zone with a time delay with respect to the internal testing unit, and the marking devices execute by means of a coordinate control action a relative motion on the carriage or on the conveyor carts; or the conveyor carts, with the fixedly installed marking devices, execute a relative motion with respect to the carriage in correspondence with the location of the thus-determined defective sites of the pipes, in opposition to or in the advancing direction of the carriage or carts.

The use of an internal testing unit with a forward and rearward exchangeable wheel set, with a fixed adjustment of the drive roller and the two supporting rollers, as well as the installation of delivery tables with a roller or belt guide means for the internal testing unit provide a substantial simplification with respect to the constructional expenditure and operation, as compared with conventional pipe testing installations. To change the pipe testing installation over to a different pipe diameter, it is merely necessary to exchange the two running gears of the internal testing unit against running gears with a fixed setting of the drive roller and the supporting rollers adapted to the new pipe diameter.

The invention will be explained in detail below with reference to an embodiment illustrated in the drawings wherein.

The pipe testing installation for determining surface defects or flaws of the inner and outer pipe walls and/or core defects of the pipe wall is constructed as a two-lane testing system with two testing zones 1, 2 of identical construction. In a modification of the illustrated embodiment, it is possible to equip the pipe testing installation with three and more testing zones.

Figure 1A:
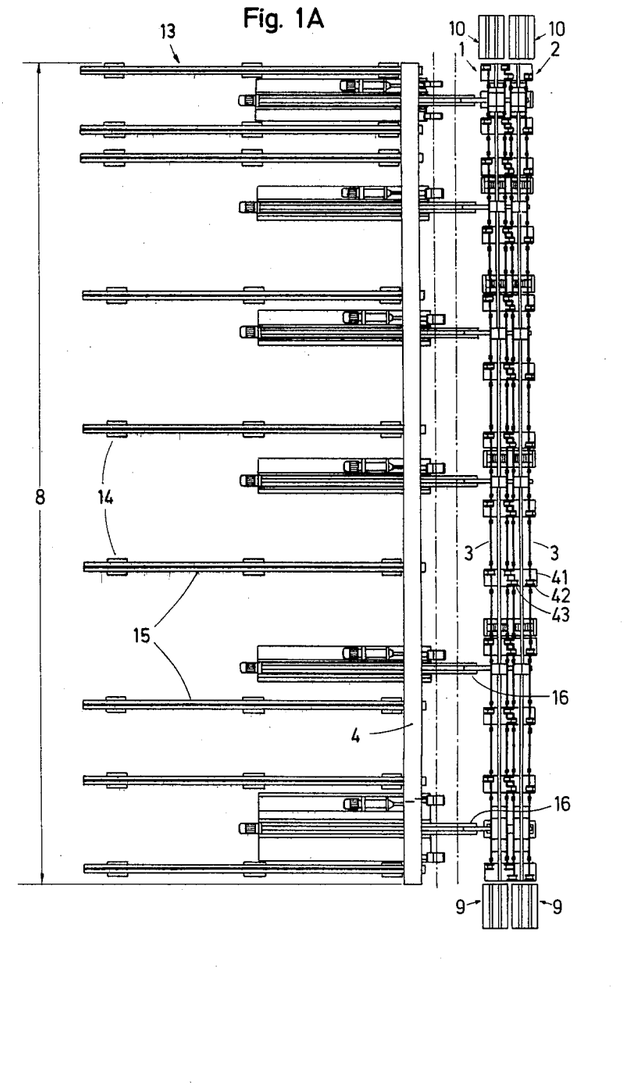
FIGS. 1A and 1B show top views of the pipe testing installation of this invention, respectively in an enlarged, schematic representation.
Figure 1B:
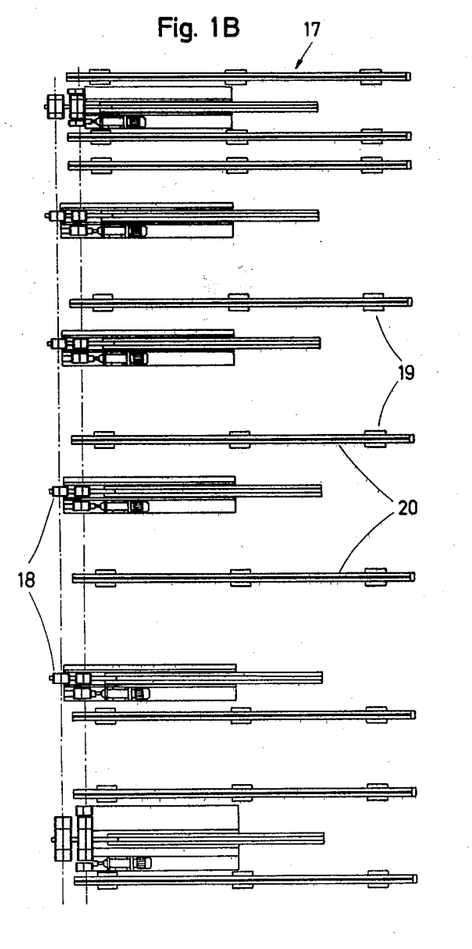

The primary structural elements of the two testing zones 1, 2 are a rotary roller track 3 for the revolving drive of the pipe 4 to be tested; an internal testing unit 7 movable in the direction of the longitudinal pipe axis 5—5 on the inner wall 6 of the pipe 4; delivery tables 9, 10 adjustable to the pipe length 8 at the two end faces of the pipe 4 to accommodate the internal testing unit 7 during pipe change; an external testing unit 12 movable along the outer pipe wall 11; as well as conveying means for the introduction and removal of the pipes 4 into and out of the testing zones 1, 2, respectively.

The pipes 4 to be tested are stored on a feed table 13 arranged along the outwardly oriented longitudinal side of the first testing zone 1 and made up of trestles 14 arranged at mutual spacings and comprising supports 15 inclined in the direction toward the testing zone 1. Two pipes 4 are respectively introduced into the testing zones 1, 2 by hydraulically operated lifting bars 16. The tested pipes 4 are transported by the lifting bars 16 to a discharge table 17 on the outwardly oriented longitudinal side of the second testing zone 2 and lifted, by pivoting arms 18, onto the discharge table 17, this discharge table consisting of spaced-apart trestles 19 with supports 20, installed with a slight downward slope from the region of the second testing zone 2 toward the outside.

Figure 3:
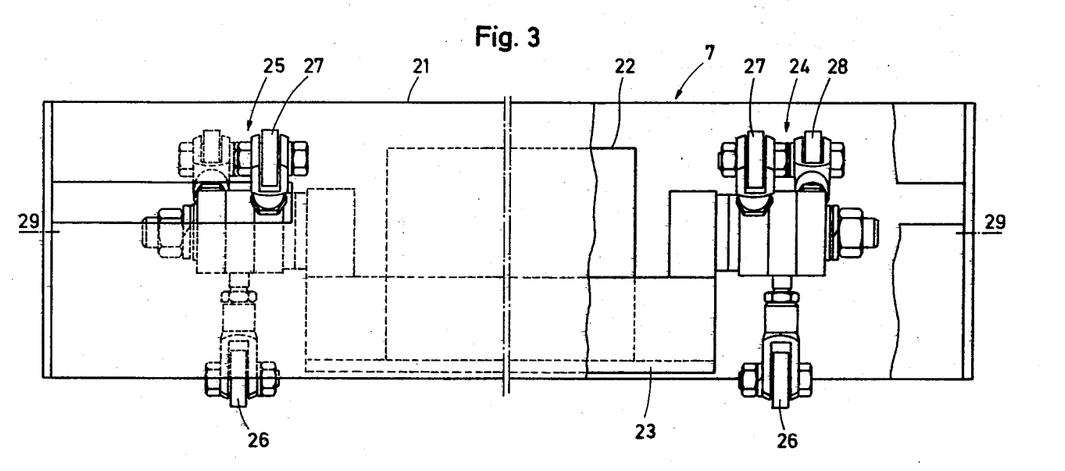
FIG. 3 shows a lateral view of the internal testing unit with a partial longitudinal sectional view of the forward running gear.
Figure 5:
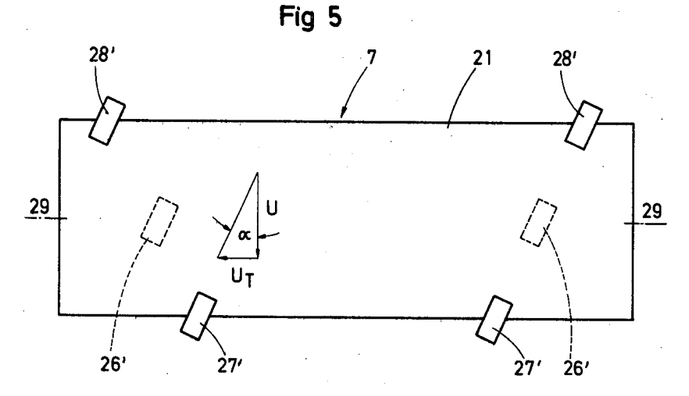
FIG. 5 shows a top view of the internal testing unit according to FIG. 3.

The internal testing unit 7 exhibits a cylindrical housing 21 accommodating noncontactual, battery-driven testing devices 22, for example eddy current testing coils. The surface defects detected by the testing devices 22, primarily cracks in the inner pipe wall 6, are transmitted by a transmitter, not shown, to a device for evaluating the surface defects which is located on the outside and is not illustrated. The housing 21 of the internal testing unit 7 is arranged on a running gear frame 23 with a forward running gear and a rearward running gear 24 and 25, respectively. The running gears 24, 25 consist of a drive roller 26 and two supporting rollers 27, 28 arranged at a spacing of 120° with respect to the drive roller, these rollers assuming a driving position 26', 27', 28' with a clearance angle $\alpha$ obliquely to the longitudinal axis 5—5 of the pipe 4 to be tested and/or to the longitudinal axis 29—29 of the testing unit 7; these rollers run along the inner pipe wall 6 and are driven by the revolving motion of the pipe 4 (FIG. 5).

The internal testing unit 7 travels in the longitudinal direction of the pipe eccentrically to the longitudinal pipe axis 5—5 through the lower region of the pipe 4 to be tested with a translatory velocity component $u_T$ dependent on the clearance angle $\alpha$ of the drive roller 26 and the supporting rollers 27, 28 of the running gears 24, 25, resulting from the rotary velocity u of the pipe 4 to be tested.

The drive roller 26 of the running gears 24, 25 is arranged in the longitudinal plane of symmetry of the internal testing unit 7 and assumes a radial fixed setting with respect to the longitudinal axis 29—29 of the internal testing unit 7, and the supporting rollers 27, 28 of the running gears 24, 25 are adjustable in correspondence with the internal diameter 30 of the pipe 4 to be tested, radially to the longitudinal axis 29—29 of the testing unit 7.

Figure 4:
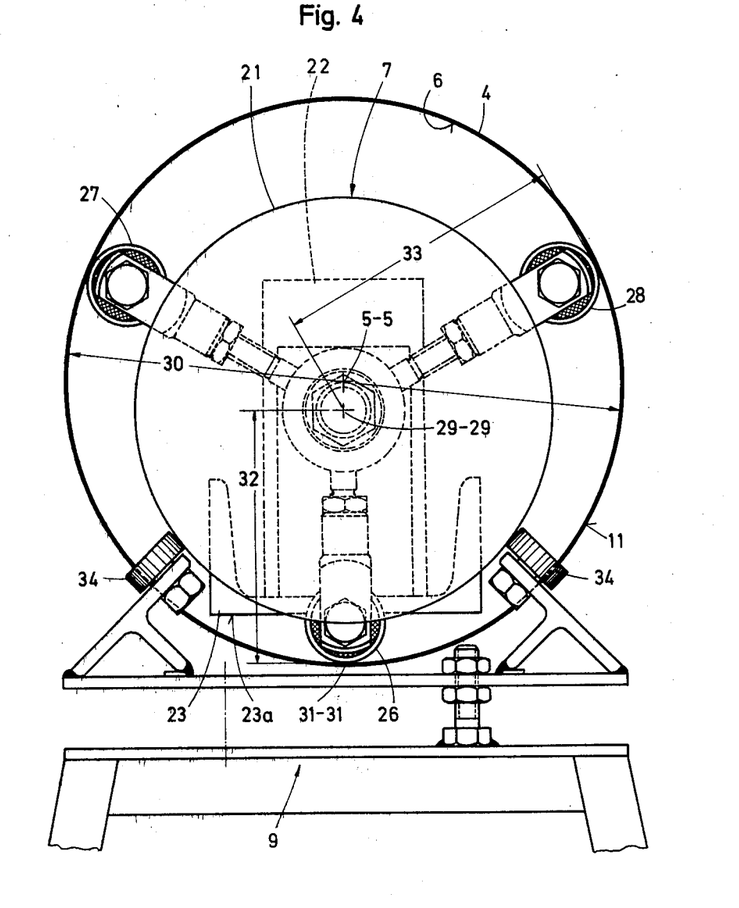
FIG. 4 shows a front view of a delivery table with a roller guide means for the parked internal testing unit, in the direction of arrow IV in FIG. 2.

By the radial fixed adjustment of the drive roller 26 of the running gears 24, 25 pertaining to the internal testing unit 7, it is ensured that the distance between the underside 23a of the running gear frame 23 and the respectively lowermost generatrix 31—31 of the revolving pipe 4 to be tested, which generatrix extends in the longitudinal direction, and thus the measuring distance between the testing unit 7 and the inner pipe wall 6 remains constant (FIG. 4).

In a modification of the above-described arrangement, the internal testing units 7 can be equipped with exchangeable running gears 24, 25 for varying pipe diameters 30, with a fixed adjustment of the drive position 26', 27', 28', as well as of the radial spacings 32, 33 of the drive roller 26 and the supporting rollers 27, 28 with respect to the central longitudinal axis 29—29 of the testing unit 7.

The parking stations fashioned as delivery tables 9, 10 at both ends of the testing zones 1, 2 are provided with a roller guide means 34 to accommodate the housing 21 of the internal testing unit 7 during pipe change. A lifting cylinder 35, operated by a pressure medium and equipped with a lifting rod 36, is arranged on the delivery tables 9, 10, this lifting rod imparting to the parking internal testing unit 7 a starting motion in the direction toward the pipe 4 to be tested (FIG. 2).

In a modified arrangement of the testing installation, a cylinder 37 for lifting the end 38 of the roller guide means 34 facing away from the testing specimen is installed in the delivery tables 9, 10; the roller guide means is constructed as a pivoting guide means in this embodiment. By lifting the roller guide means 34 into the position 34', the internal testing unit 7 is moved from the delivery table 9 or 10 into the pipe 4 to be tested.

Furthermore, the delivery tables 9, 10 can be equipped with a further cylinder 39 to lift the end 40 of the roller guide means 34 adjacent to the testing specimen, in order to obtain the objective that the internal testing unit 7 is moved onto the delivery tables 9, 10 to such an extent that sufficient safety distance is provided with respect to the roller tracks 3 and thereby a damaging of the internal testing unit 7 during introduction and removal of the pipes 4 into and/or from the testing zones 1, 2 is avoided.

Figure 2:
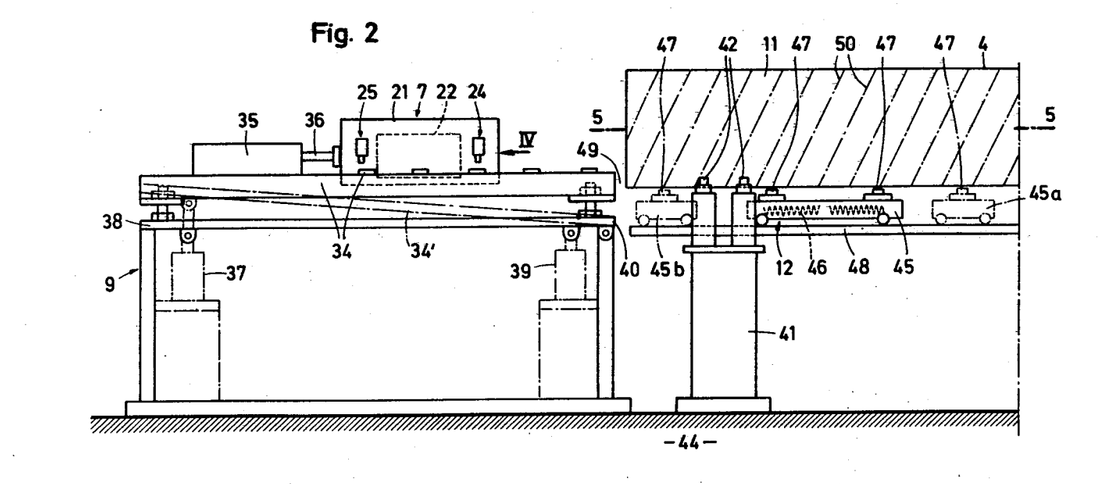
FIG. 2 shows a lateral view of a delivery table of a testing zone.
Figure 4A:
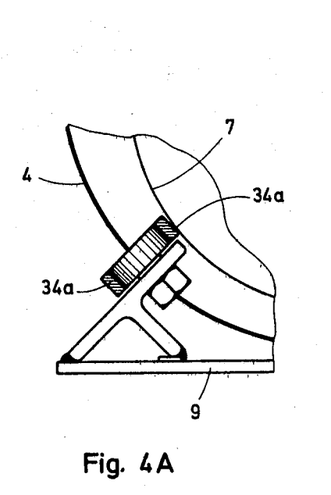
FIG. 4A shows a fragmentary frontal view of a delivery table with a roller belt guide for the internal testing unit.

In a further embodiment of the testing installation, the roller guide means 34 of the delivery tables 9, 10 according to FIGS. 2 and 4 are replaced by a roller belt guide with two motor-driven roller belts 34a, 34a which, during pipe change, serve as the parking station for the internal testing unit 7 and move the latter out of and into the pipe 4 to be tested (FIG. 4A).

The delivery tables 9, 10 are movable in the direction of the testing zones 1, 2.

The rotary roller track comprises bearing blocks 41 arranged in spaced-apart relationship, for motor-driven wobble disks 42, 43 to provide a rotary drive for the pipes 4 to be tested. The wobble disks 42, 43 are horizontally and vertically adjustable in the perpendicular transverse plane of the pipes 4 to be tested, in order to set a predetermined testing distance between the external testing unit 12 and the outer wall 11 of the pipes 4 to be tested, which pipes exhibit differing diameters. The bearing blocks 41 of the rotary roller track 3 are displaceable on the base member 44 in the direction of the testing zones 1, 2.

The external testing unit 12 comprises a carriage 45 with installed testing devices, for example eddy current testing coils 46, as well as marking devices movable by a motor on the carriage 45, such as paint spray guns 47 to identify the inner and outer defects and optionally core defects of the pipe 4 to be tested, this identification being provided on the outer pipe wall 11. The motor-driven carriage 45 is movable underneath the pipe 4 to be tested in the zone of the vertical longitudinal plane of symmetry of the pipe on a running track 48 along the testing zone 1. The surface defects of the pipe wall detected by the external testing unit 12 are transmitted via cable connections or in a wireless fashion via a transmitter to the device for evaluating the surface defects, mentioned in connection with the internal testing unit 7, to which evaluating device a control means is connected for the paint spray guns 47 on the carriage 45.

A modified embodiment of the external testing unit 12 of the pipe testing installation consists of a carriage 45 with built-in testing devices 46 for detecting the defects of the pipes 4, as well as a separate conveyor cart 45a, 45b moving in front of and behind the carriage 45 and comprising optionally motor-driven marking devices 47 for identifying the defects of the pipes 4 (FIG. 2).

The conveyor carts 45a, 45b for the marking devices 47 can be coupled with the carriage 45 or can be equipped with their own motor drive mechanism.

The testing installation operates as follows:

Respectively two pipes of the pipes 4 to be tested, having possibly differing lengths and stored with their one end facing the delivery table 9 flush on the feed table 13, are inserted by the lifting bars 16 in the rotary roller tracks 3 of the two testing zones 1, 2 of the pipe testing installation, adjusted to the pipe dimensions to be tested. Subsequently, the delivery tables 9, 10 are moved toward the ends of the testing zones 1, 2.

At this point in time, the pipes 4 to be tested are accelerated by the rotary roller tracks 3 to a revolving speed corresponding to the testing velocity. Subsequently the internal testing units 7, parked, for example, on the delivery tables 9, are advanced in the direction toward the pipes 4 to be tested by means of the lifting rods 36 of the lifting cylinders 35 or by the roller belts 34a, 34a, set into motion by an electric motor, and the internal testing units 7 enter, with the housing 21, on the roller guide means 34 or on the roller belts 34a, 34b, into the test pipes 4. As soon as the housing 21 of the internal testing units passes over the parting line 49 between the roller guide means 34 or the roller belts 34a and the revolving pipe, the internal testing units 7 are moved forward in the direction of the longitudinal pipe axis 5—5 by the revolving motion of the pipes 4 to be tested; in this connection, the advancing speed $u_T$ of the internal testing units 7 resulting from the peripheral velocity u of the pipe 4 to be tested is dependent on the angular position $\alpha$ of the drive roller 26, as well as of the supporting rollers 27, 28 of initially the forward running gear 24 and, after the complete entrance of the internal testing units 7 into the pipes 4, also of the rearward running gear 25, with respect to the longitudinal pipe axis 5—5. With a time delay with respect to the internal testing units 7, the carriages 45 of the external testing units 12, parked at the end of the testing zones 1, 2 adjacent the delivery table 9, are set into motion with the same advancing speed as the internal testing units 7.

The internal testing units 7 pass through the pipes 4 to be tested in the longitudinal direction and exit at the other end of the testing zones 1, 2 from the rotary roller track 3 onto the roller guide means 34 or the roller belts 34a of the delivery tables 10. When using delivery tables 10 with roller belts 34a, the internal testing units 7 moving out of the tested pipes 4 initially push the roller belts 34a forward by a certain belt length, these roller belts being connected with an overrunning clutch to an electric motor drive mechanism. Thereafter, the drive motor of the roller belts 34a is turned on, and the roller belts then convey the internal testing units 7 to a stop on the delivery tables 10. The carriages 45 of the external testing units 12 travel, at a certain distance behind the internal testing units 7, along the outer pipe wall 11 underneath the pipes 4. The entire surfaces of the inner wall 6 and the outer wall 1 of the two pipes 4 are examined for surface defects, i.e. essentially crack formations, by the internal testing units 7 and the external testing units 12 along helical testing paths 50. The data measured by the internal and external testing units 7, 12 are transmitted to an evaluating and control device which latter controls the paint spray guns 47 arranged on the carriages 45 or on the conveyor carts 45a, 45b of the external testing units 12, to identify the inner and outer surface defects on the outer pipe wall 11.

The positionally accurate marking of the internal defects, external defects, and possibly core defects, determined by the internal testing units 7 and the external testing units 12 in the pipes 4 to be tested, effected on the outer pipe wall 11, is conducted in such a way that the external testing units 12 move along the testing zones 1, 2 at the same advance velocity as the internal testing units 7, with a time delay with respect to the internal testing units 7, and that the marking devices 47, by means of a coordinate control, execute a relative motion on the carriage 45 or on the conveyor carts 45a, 45b, or that the conveyor carts 45a, 45b with the fixedly installed marking devices 47 execute a relative motion with respect to the carriage 45 in correspondence with the position of the thus-determined defect sites of the pipes 4, in opposition to or in the advancement direction of the carriage or carts 45, 45a, 45b.

For example, if the internal testing unit 7 has detected a defect on the inner wall 6 of the pipe 4 to be tested, then the paint spray gun 47 responsible for identifying the internal defects on the carriage 45 must be controlled by the control device arranged outside of the testing zone in such a way that the defect site is marked at the correct location on the outer wall 11 of the revolving pipe 4. This is effected in such a way that the paint spray gun 47 is set into motion in opposition to the advancing movement of the carriage 45 on the latter, with the same advancing speed, so that the relative advancing motion of the paint spray gun 47 with rspect to the pipe 4 is reduced to the value of 0 for a short time, and the determined defect site is marked positionally accurately on the outer pipe wall 11 in response to a control command from the control device, with the aid of the paint spray gun 47, as soon as the defect site passes through the marking plane of the paint spray gun 47.

To remove the tested pipes 4 from the testing zones 1, 2, the rotary roller tracks 3 are braked, and the tested pipes 4 are transported to the discharge table 17 by the lifting bars 16 as well as the pivoting arms 18. Subsequently, two further pipes 4 are taken by the lifting bars 16 from the feed table 13 and introduced for testing purposes into the rotary roller tracks 3 of the two testing zones 1, 2. A new testing procedure is thus initiated wherein the internal and external testing units 7, 12, after reversing the direction of rotation of the driven wobble disks 42, 43 of the rotary roller tracks 3, are now passing in the reverse direction from the delivery tables 10 to the delivery tables 9 through the two testing zones 1, 2.

What is claimed is:

1. Testing installation for pipes to determine surface defects and core defects, characterized by at least one testing zone (1, 2) comprising a rotary roller track (3) for rotatingly driving the pipe (4) to be tested, an internal testing unit (7) movable in a direction along the longitudinal axis of the pipe, within the pipe (4), parking stations (9, 10) adjustable to the pipe length at both ends of the testing zone (1, 2) for accommodating the internal testing unit (7) during pipe change, an external testing unit (12) movable along the outer pipe wall (11), and conveying devices (16) for the introduction and for the removal of the pipes (4) into and from the testing zone (1, 2), respectively, wherein the internal testing unit (7) is a cylindrical housing (21) equipped with built-in contactless testing devices (22) and arranged on a running gear frame (23) with a forward running gear and a rearward running gear (24, 25), and wherein the running gears (24, 25) consist of a drive shaft (26) and two supporting rollers (27, 28) assuming a driving position (26', 27', 28') obliquely to the longitudinal axis (5—5) of the pipe (4) to be tested, traveling on the inner pipe wall (6), and being driven by the revolving motion of the pipe (4) to be tested, which latter is located between the parking stations (9, 10).

2. Testing installation according to claim 1, characterized in that the drive shaft (26) is arranged in the central longitudinal plane of the internal testing unit (7) and has a radial fixed adjustment with respect to the longitudinal axis (29—29) of the internal testing unit (7); and that the supporting rollers (27, 28) are adjustable radially with respect to the longitudinal axis (29—29) of the testing unit (7) in correspondence with the internal diameter (30) of the pipe (4) to be tested.

3. Testing installation according to claim 2, characterized by internal testing units (7) with exchangeable running gears (24, 25) for varying pipe diameters (30) with a fixed setting of the driving position (26', 27', 28') as well as of the radial spacings of the drive roller (26) and the supporting rollers (27, 28) with respect to the longitudinal axis (29—29) of the internal testing unit (7).

4. Testing installation according to claim 1, characterized in that the parking stations are fashioned as delivery tables (9, 10) with a roller guide means (34) for the accommodation of the internal testing unit (7), as well as with an advancing means for the testing unit (7).

5. Testing installation according to claim 4, characterized by a lifting cylinder (35) arranged on the delivery tables (9, 10) and comprising said means for advancing the internal testing unit (7).

6. Testing installation according to claim 4, characterized by a lifting device (37) for lifting the end (38) of the roller guide means (34), fashioned as a pivoting guide, for the internal testing unit (7), which end faces away from the pipe (4) to be tested.

7. Testing installation according to claim 6, characterized by an additional lifting means (39) for lifting the end (40) of the roller guide means (34) of the internal testing unit (7), which end is adjacent to the pipe (4) to be tested.

8. Testing installation according to claim 1, characterized in that the parking stations exhibit delivery tables (9, 10) with a roller belt guide for the internal testing unit (7), and that the two roller belts (34a, 34a) of the belt guide are equipped with a motor drive.

9. Testing installation according to claim 1, characterized by controlling the forward and reverse motions of the internal testing unit (7) by a reversal of the direction of rotation of motor-driven wobble disks (42, 43) of the rotary roller track (3) that contact the pipe to be tested.

10. Testing installation according to claim 1, characterized by a fixed setting of the measuring distance, independent of the diameter (30) of the pipe (4) to be tested, between the testing devices (22) of the internal testing unit (7) and the inner wall (6) of the pipe (4) to be tested, by way of the radial fixed adjustment of the drive roller (26) of the running gears (24, 25) of the internal testing unit (7).

11. Testing installation according to claim 1, characterized in that the external testing unit (12) comprises a carriage (45) with built-in testing devices (eddy current testing coils 46), as well as marking devices (paint spray guns 47) movable by a motor for marking the internal and external defects and any core defects of the pipe (4) to be tested; and that the motor-driven carriage (45) is movable underneath the pipe (4) in the zone of the vertical longitudinal plane of symmetry thereof along the testing zone (1, 2).

12. Testing installation according to claim 1, characterized in that the external testing unit (12) comprises a carriage (45) with built-in testing devices (46) for determining the defects of the pipes (4), and a separate conveyor cart (45a, 45b) moving in front of and behind the carriage (45) and exhibiting optionally motor-driven marking devices (47) for identifying the defects.

13. Testing installation according to claim 12, characterized in that the conveyor carts (45a, 45b) for the marking devices (47) are coupled with the carriage (45) for the testing devices (46).

14. Testing installation according to claim 12, characterized by a separate motor driven mechanism of the conveyor carts (45a, 45b) for the marking devices (47).

* * * * *